(12) United States Patent
Hata et al.

(10) Patent No.: US 10,232,320 B2
(45) Date of Patent: Mar. 19, 2019

(54) HOLLOW-FIBER MEMBRANE BLOOD PURIFICATION DEVICE

(71) Applicant: ASAHI KASEI MEDICAL CO., LTD., Tokyo (JP)

(72) Inventors: Yosuke Hata, Tokyo (JP); Chiharu Kawano, Tokyo (JP); Ryoko Hori, Tokyo (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 15 days.

(21) Appl. No.: 15/514,863

(22) PCT Filed: Sep. 29, 2015

(86) PCT No.: PCT/JP2015/077619
§ 371 (c)(1),
(2) Date: Mar. 28, 2017

(87) PCT Pub. No.: WO2016/052567
PCT Pub. Date: Apr. 7, 2016

(65) Prior Publication Data
US 2017/0209836 A1     Jul. 27, 2017

(30) Foreign Application Priority Data

Sep. 29, 2014  (JP) .................... 2014-199266

(51) Int. Cl.
*A61M 1/16* (2006.01)
*B01D 63/02* (2006.01)
(Continued)

(52) U.S. Cl.
CPC ............ *B01D 69/08* (2013.01); *B01D 63/02* (2013.01); *B01D 67/0088* (2013.01);
(Continued)

(58) Field of Classification Search
None
See application file for complete search history.

(56) References Cited

U.S. PATENT DOCUMENTS

| | | |
|---|---|---|
| 2005/0063859 A1 | 3/2005 | Masuda et al. |
| 2008/0000830 A1 | 1/2008 | Mabuchi et al. |

(Continued)

FOREIGN PATENT DOCUMENTS

| | | |
|---|---|---|
| EP | 1813297 A1 | 8/2007 |
| ES | 2367512 A1 | 11/2011 |

(Continued)

OTHER PUBLICATIONS

International Search Report issued in International Application No. PCT/JP2015/077619, dated Dec. 1, 2015.

(Continued)

*Primary Examiner* — Krishnan S Menon
(74) *Attorney, Agent, or Firm* — Greenblum & Bernstein, P.L.C.

(57) ABSTRACT

The present invention provides a hollow-fiber membrane blood purification device obtained by filling a container with a hollow-fiber membrane, in which the hollow-fiber membrane contains a hydrophobic polymer, a hydrophilic polymer and a lipid-soluble substance; the amount of the lipid-soluble substance on the inner surface of the hollow-fiber membrane is 10 mg/m² or more and 300 mg/m² or less; and the oxygen transmission rate of the container is $1.8 \times 10^{-10}$ cm³·cm/(cm²·s·cmHg) or less.

8 Claims, 2 Drawing Sheets

(51) Int. Cl.
   *B01D 65/02* (2006.01)
   *B01D 67/00* (2006.01)
   *B01D 69/02* (2006.01)
   *B01D 69/08* (2006.01)
   *B01D 71/12* (2006.01)
   *B01D 71/16* (2006.01)
   *B01D 71/58* (2006.01)
   *B01D 71/68* (2006.01)

(52) U.S. Cl.
   CPC ............ *B01D 71/12* (2013.01); *B01D 71/58* (2013.01); *B01D 71/68* (2013.01); *A61M 1/16* (2013.01); *B01D 65/022* (2013.01); *B01D 69/02* (2013.01); *B01D 71/16* (2013.01); *B01D 2313/20* (2013.01); *B01D 2323/46* (2013.01); *B01D 2325/44* (2013.01)

(56) References Cited

U.S. PATENT DOCUMENTS

| | | | |
|---|---|---|---|
| 2008/0044643 A1 | 2/2008 | Yokota et al. | |
| 2008/0087599 A1* | 4/2008 | Mabuchi | A61L 2/087 |
| | | | 210/500.23 |
| 2014/0158611 A1* | 6/2014 | Satoh | A61M 1/16 |
| | | | 210/500.23 |
| 2016/0354728 A1* | 12/2016 | Hori | B01D 63/02 |

FOREIGN PATENT DOCUMENTS

| | | |
|---|---|---|
| JP | 2005-95270 | 4/2005 |
| JP | 2006-296931 A | 11/2006 |
| JP | 2008-161247 | 7/2008 |
| JP | 2009-101591 | 5/2009 |
| JP | 2013-009761 | 1/2013 |
| JP | 2013-094525 | 5/2013 |
| JP | 2014-161631 | 9/2014 |
| JP | 2015-116211 | 6/2015 |
| JP | 2015-116212 | 6/2015 |
| JP | 2015-116214 | 6/2015 |
| WO | 2006/016573 | 2/2006 |
| WO | 2006/016575 | 2/2006 |

OTHER PUBLICATIONS

International Preliminary Report on Patentability in International Application No. PCT/JP2015/077619, dated Apr. 4, 2017.
Supplemental European Search Report issued for European Application No. 15846799.3 dated Aug. 22, 2017.

* cited by examiner

[Figure 1]
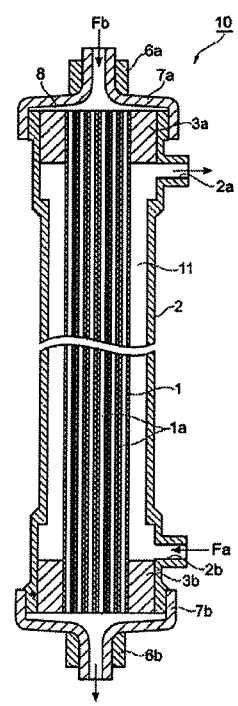

[Figure 2]
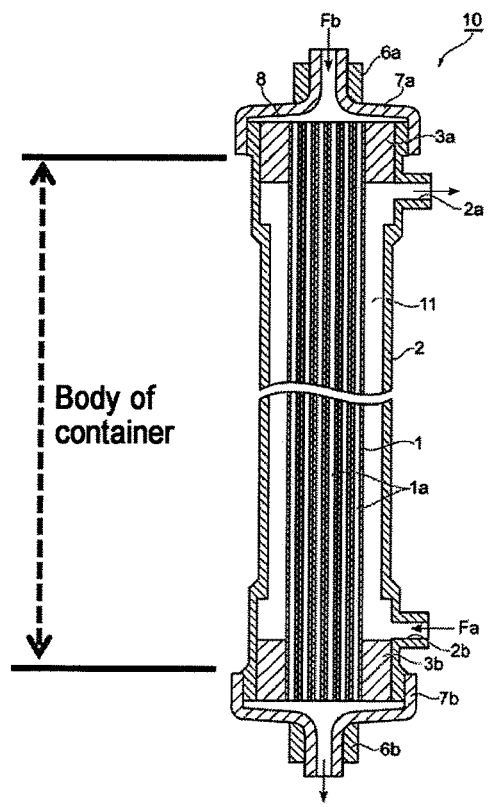
[Figure 3]
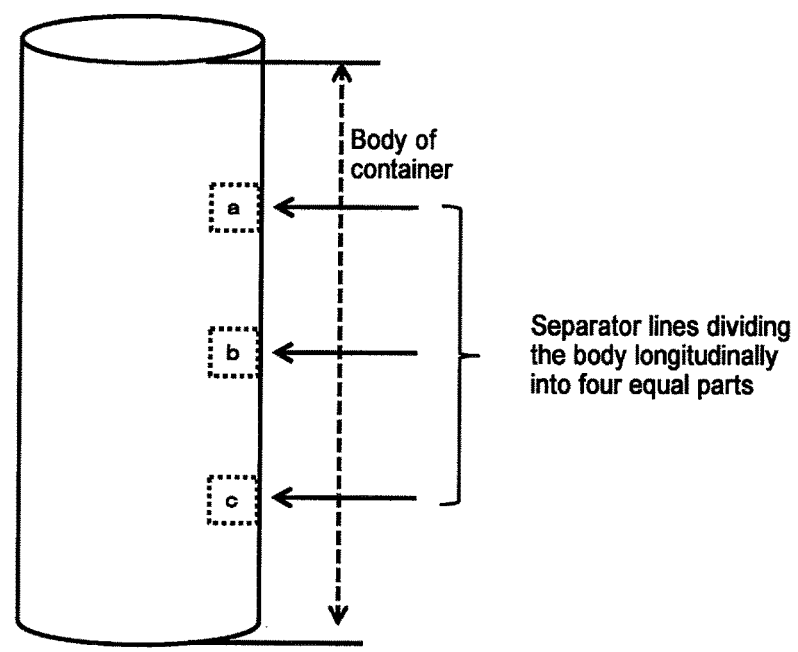

HOLLOW-FIBER MEMBRANE BLOOD PURIFICATION DEVICE

TECHNICAL FIELD

The present invention relates to a hollow-fiber membrane blood purification device.

BACKGROUND ART

In the extracorporeal circulation therapy, a hollow-fiber membrane blood purification device using a hollow-fiber membrane as a selective separation membrane has been widely used. A hollow-fiber membrane blood purification device is used, for example, in hemodialysis, which is used as a maintenance therapy for chronic renal failure patients; in hemofiltration and hemodiafiltration, which are used as an acute blood purification therapy and a maintenance therapy for acute and chronic renal failure patients; in continuous hemodialysis, continuous hemofiltration and continuous hemodiafiltration, which are used as an acute blood purification therapy for patients with serious conditions such as acute renal failure and sepsis; and oxygenation to the blood and plasmapheresis during open heart surgery.

Recently, in order to control mechanical strength, chemical stability and permeability, a selective separation membrane made of a polysulfone resin or a cellulose acetate resin has been spread at a high speed. Since the polysulfone resin and cellulose acetate resin are hydrophobic polymers, a selective separation membrane consisting of the polysulfone resin or cellulose acetate resin alone is extremely insufficient in hydrophilicity of the membrane surface. Because of this, the selective separation membrane has drawbacks in that blood compatibility is low; the membrane interacts with blood components, easily causing blood coagulation; and protein components absorb to the membrane, easily decreasing permeability.

To make up for these drawbacks, attempts have been made to provide a selective separation membrane with blood compatibility by using a hydrophilic polymer, such as polyvinylpyrrolidone (PVP), polyvinyl alcohol and polyethylene glycol, in a selective separation membrane, in addition to a hydrophobic polymer. For example, a method of improving blood compatibility by enhancing hydrophilicity of the membrane by producing a membrane from a spinning dope for membrane production containing a hydrophobic polymer and a hydrophilic polymer blended together; and a method of providing blood compatibility by coating the membrane with the hydrophilic polymer, in a dry-wet membrane production step, for example, by producing a membrane using a hollow-portion internal liquid containing a hydrophilic polymer, followed by drying; or by bringing the produced membrane into contact with a solution containing a hydrophilic polymer, followed by drying, are known.

In addition, recently, in order to mitigate oxidative stress markedly observed in long-term dialysis patients, a dialyzer provided with a lipid-soluble substance having antioxidative property has been developed. For example, an attempt to remove a causative substance of oxidative stress, i.e., a peroxide, by using a hollow-fiber membrane and an attempt to recover an antioxidative effect of a living body, have been made.

Patent Literatures 1 and 2 disclose a blood purification device containing a lipid-soluble vitamin such as vitamin E having various physiological actions such as in-vivo antioxidative action, biomembrane stabilizing action and platelet-aggregation suppressive action. It is known that one of the hydrophobic polymers, a polysulfone resin, has high affinity for a lipid-soluble vitamin, which is effective for suppressing oxidative stress induced by extracorporeal blood circulation; and that a lipid-soluble vitamin is easily immobilized to the surface of a hollow-fiber membrane.

Since a blood purification device is medical equipment, sterilization is required. As a sterilization method, radiation sterilization using e.g., γ ray and an electron beam has been mainly used. A hollow-fiber membrane blood purification device sterilized with a radial ray has a problem in that a lipid-soluble substance is e.g., decomposed and degraded by a peroxide substance produced by sterilization, with the result that antioxidative property and blood compatibility decrease.

As a method for preventing performance deterioration of a hollow-fiber membrane, Patent Literatures 3 and 4 disclose a method for preventing oxidative degradation of a hollow-fiber membrane due to sterilization by controlling the oxygen concentration within a hollow-fiber membrane blood purification device and the moisture content of the hollow-fiber membrane during sterilization.

CITATION LIST

Patent Literature

Patent Literature 1: Japanese Patent Laid-Open No. 2013-9761
Patent Literature 2: Japanese Patent Laid-Open No. 2013-94525
Patent Literature 3: International Publication No. WO 2006/016573
Patent Literature 4: International Publication No. WO 2006/016575

SUMMARY OF INVENTION

Technical Problem

However, in the methods disclosed in Patent Literatures 3 and 4, if the oxygen concentration and the moisture content of a hollow-fiber membrane during sterilization change, the water-permeability of a hollow-fiber membrane varies. Thus, the oxygen concentration and the moisture content of a hollow-fiber membrane during sterilization must be accurately controlled, and thus productivity is low. As a result of investigation by the present inventors, it was further found that if a lipid-soluble substance is contained in a hollow-fiber membrane, the range of water-permeability to be controlled is further narrowed.

Accordingly, it has been strongly desired to develop a hollow-fiber membrane blood purification device having high antioxidative property and blood compatibility, containing not only a hydrophobic polymer and a hydrophilic polymer but also a lipid-soluble substance and successfully suppressing deterioration of antioxidative property due to sterilization without accurately controlling the moisture content and water-permeability.

It is also known that a lipid-soluble substance deteriorates by light irradiation. For example, if a blood purification device is stored under fluorescent light, antioxidative property is known to deteriorate with time. Accordingly, it has been desired to develop a hollow-fiber membrane blood purification device having high antioxidative property and blood compatibility even if the device is exposed to light such as fluorescent light.

An object of the present invention is to provide a hollow-fiber membrane blood purification device having satisfactory blood compatibility and stable antioxidative property.

Solution to Problem

The present inventors conducted intensive studies to solve the above problems and, as a result, found that the problems can be solved by a hollow-fiber membrane blood purification device having the amount of the lipid-soluble substance on the inner surface of the hollow-fiber membrane and the oxygen transmission rate of a container within predetermined ranges. Based on the finding, the present invention was accomplished.

The present invention is more specifically as follows.

[1]

A hollow-fiber membrane blood purification device obtained by filling a container with a hollow-fiber membrane, in which the hollow-fiber membrane contains a hydrophobic polymer, a hydrophilic polymer and a lipid-soluble substance, an amount of the lipid-soluble substance on the inner surface of the hollow-fiber membrane is 10 mg/m$^2$ or more and 300 mg/m$^2$ or less, and an oxygen transmission rate of the container is $1.8 \times 10^{-10}$ cm$^3$·cm/(cm$^2$·s·cmHg) or less.

[2]

The hollow-fiber membrane blood purification device according to [1], in which the absorbance of the body of the container at a wavelength of 350 nm is 0.35 or more and 2.00 or less.

[3]

The hollow-fiber membrane blood purification device according to [1] or [2], in which the hydrogen peroxide concentration of the initial effluent (100 mL) when saline is passed through is 10 ppm or less.

[4]

The hollow-fiber membrane blood purification device according to any one of [1] to [3], wherein the hollow-fiber membrane blood purification device is housed in a sterilizing bag having an oxygen transmission rate of $1.5 \times 10^{-10}$ cm$^3$·cm/(cm$^2$·s·cmHg) or less.

[5]

The hollow-fiber membrane blood purification device according to any one of [1] to [4], in which the lipid-soluble substance is a lipid-soluble vitamin.

[6]

The hollow-fiber membrane blood purification device according to any one of [1] to [5], in which the hydrophobic polymer has a solubility parameter $\delta$(cal/cm$^3$)$^{1/2}$ of 13 or less.

[7]

The hollow-fiber membrane blood purification device according to any one of [1] to [6], in which the hydrophobic polymer is at least one selected from the group consisting of polysulfone, polyethersulfone and cellulose triacetate.

[8]

The hollow-fiber membrane blood purification device according to any one of [1] to [7], in which the hydrophilic polymer is polyvinylpyrrolidone.

Advantageous Effects of Invention

The present invention can provide a hollow-fiber membrane blood purification device having satisfactory blood compatibility and stable antioxidative property.

BRIEF DESCRIPTION OF DRAWINGS

FIG. 1 shows a typical hollow-fiber membrane blood purification device.

FIG. 2 shows the body of the typical hollow-fiber membrane blood purification device.

FIG. 3 shows the portions a, b, c, of the body of a container subjected to measurement of absorbance at a wavelength of 350 nm.

DESCRIPTION OF EMBODIMENTS

Now, an embodiment for carrying out the present invention (hereinafter referred to as the embodiment) will be more specifically described. Note that, the present invention is not limited to the following embodiments and can be carried out by modifying it in various ways within the scope of the invention.

<Hollow-Fiber Membrane Blood Purification Device>

The hollow-fiber membrane blood purification device of the embodiment is a hollow-fiber membrane blood purification device consisting of a container filled with a hollow-fiber membrane. The hollow-fiber membrane contains a hydrophobic polymer, a hydrophilic polymer and a lipid-soluble substance, and the amount of the lipid-soluble substance on the inner surface of the hollow-fiber membrane is 10 mg/m$^2$ or more and 300 mg/m$^2$ or less and the oxygen transmission rate of the container is $1.8 \times 10^{-10}$ cm$^3$·cm/(cm$^2$·s·cmHg) or less.

The hollow-fiber membrane blood purification device of the embodiment is preferably used in e.g., a hemodialyzer, a blood hemofilter and a hemodiafiltration device, and more preferably used in persistent use of these, i.e., a continuous hemodialyzer, a continuous hemofilter and a continuous hemodiafiltration device.

A typical hollow-fiber membrane blood purification device is shown in FIG. 1. The design of the device may be appropriately modified within a desired range of the embodiment.

The hollow-fiber membrane that is to be integrated in the hollow-fiber membrane blood purification device may be crimped in view of permeability.

<Hollow-Fiber Membrane>

In the embodiment, the "hollow-fiber membrane" is a hollow-fiber membrane for use in blood treatment.

The shape of the hollow-fiber membrane defined by e.g., the inner diameter, thickness and length can be arbitrarily controlled. For example, the inner diameter may be 100 μm or more and 300 μm or less. The thickness is 10 μm or more and 100 μm or less. The length may be 10 cm or more and 40 cm or less.

The hollow-fiber membrane is preferably a so-called asymmetric membrane having a thin dense layer (active separation layer) for attaining both of high molecular weight fractionation and high water-permeability and a porous layer (support layer) responsible for strengthening the hollow-fiber membrane.

In the embodiment, the container is filled with a hollow-fiber membrane, more specifically, with a bundle of hollow-fiber membranes formed of a plurality of hollow-fiber membranes.

In the embodiment, the hollow-fiber membrane contains a hydrophobic polymer, a hydrophilic polymer and a lipid-soluble substance.

<Hydrophobic Polymer>

In the embodiment, the "hydrophobic polymer" refers to a synthetic polymer or a natural polymer not dissolved in water or exhibiting no affinity for water.

Examples of the hydrophobic polymer include a polysulfone resin such as polysulfone, polyethersulfone and a polymer alloy of polyethersulfone-polyarylate; a methacrylate resin such as polymethyl methacrylate, polyhydroxyethyl methacrylate and a copolymer of these; a cellulose acetate resin such as cellulose triacetate and cellulose diacetate; polyacrylonitrile; polyamide; polyarylate; polycarbonate; poly(ether ether ketone); and poly(aryl ether ketone).

These can be used alone or in combination of two or more as the hydrophobic polymer.

<Solubility Parameter δ>

It is preferable that the hydrophobic polymer has a solubility parameter $(cal/cm^3)^{1/2}$ of 13 or less because affinity between the hydrophobic polymer and a lipid-soluble substance such as a lipid-soluble vitamin becomes satisfactory and the lipid-soluble substance can be easily held by a hollow-fiber membrane. The solubility parameter δ of the hydrophobic polymer is preferably 9.50 or more and 12 or less.

Solubility parameter δ is the index described, for example, in "Polymer Data Handbook, basic edition" edited by Society of Polymer Science, Japan, first edition issued by Kabushiki Kaisha Baifu-kan on Jan. 30, 1986, page 591 to 593. If the solubility parameter is high, hydrophilicity is strong; whereas if the solubility parameter is low, hydrophobicity is strong.

For example, hydrophobic polymers have the following solubility parameters δ: polymethyl methacrylate (δ=9.10), polysulfone (δ=9.90), polyhydroxyethyl methacrylate (δ=10.00), cellulose diacetate (δ=11.35) and polyacrylonitrile (δ=12.35).

Of the above hydrophobic polymers, a synthetic polymer is preferable in view of compositional uniformity; and polysulfone, polyethersulfone and cellulose triacetate are more preferable since a number of preferred clinical achievements in blood purification use are known, and are excellent and stable in view of raw material supply.

In the embodiment, as the "polysulfone resin", polysulfone and polyethersulfone having e.g., a part of the aromatic ring chemically modified are included.

Examples of the polysulfone resin include resins having repeating units represented by chemical formula (1) to (5) where n represents a degree of polymerization and may take any numerical value.

(1)

(2)

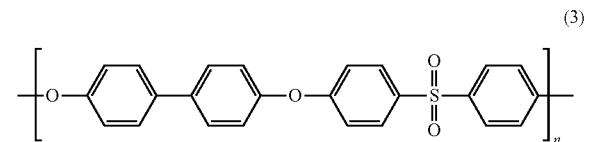

(3)

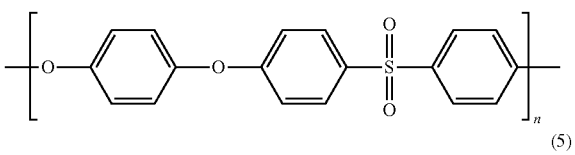

(4)

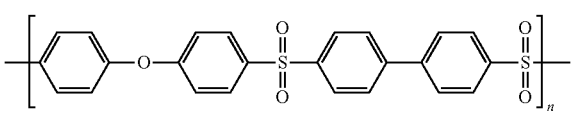

(5)

The polysulfone represented by chemical formula (1) is commercially available under a trade name of "Udel" from SOLVAY SPECIALTY POLYMERS and "Ultrason" from BASF. Each product has a plurality of types of polysulfones depending upon the degree of polymerization, however, the type is not specified.

The polyethersulfone represented by chemical formula (2) is commercially available under a trade name of "SUMIKAEXCEL PES" from SUMITOMO CHEMICAL Co., Ltd., and "Ultrason" from BASF. In view of handling and availability, the reduced viscosity of a 1 W/V % dimethylformamide solution of polyethersulfone is preferably 0.30 to 0.60 and more preferably 0.36 to 0.50.

<Hydrophilic Polymer>

In the embodiment, the "hydrophilic polymer" is a synthetic polymer or a natural polymer soluble in water or having affinity for water.

Examples of the hydrophilic polymer include polyvinylpyrrolidone (hereinafter sometimes referred to as "PVP"), polyethylene glycol, polyvinyl alcohol, polypropylene glycol and an ethylene-vinyl alcohol copolymer. In view of stability of spinning and affinity for a polysulfone resin, PVP is preferably used.

These can be used alone or in combination of two or more as the hydrophilic polymer.

A plurality of types of PVP are present depending upon the degree of polymerization. For example, under a trade name "Plasdone" available from BASF, K-15, 30 and 90 having different molecular weights are known. Any of them can be used.

<Lipid-Soluble Substance>

In the embodiment, the "lipid-soluble substance" is a substance, in general, hardly dissolved in water and soluble in alcohol, petroleum, animal/vegetable oil or other organic solvents.

Examples of the lipid-soluble substance include cholesterol; a vegetable oil such as castor oil, lemon oil and shea butter; an animal oil such as fish oil; a fatty acid ester such as a sucrose fatty acid ester and a polyglycerin fatty acid ester; a lipid-soluble vitamin such as vitamin A, vitamin D, vitamin E, vitamin K and ubiquinone; polyphenol; isoprenoid; and a hydrocarbon having a large number of molecular atoms.

These can be used alone or in combination of two or more as the lipid-soluble substance.

Examples of the lipid-soluble substance may be those obtained by appropriately chemically modifying the exemplified compounds in order to control antioxidant capacity and affinity for a hydrophobic polymer and a hydrophilic polymer.

Of these, a lipid-soluble vitamin and a lipid soluble antioxidant such as polyphenol are preferable in order to reduce oxidative stress accompanying extracorporeal blood circulation; and a lipid-soluble vitamin is preferable because no harmful effect is produced by excessive intake.

Examples of the lipid-soluble vitamin include vitamin A, vitamin D, vitamin E, vitamin K and ubiquinone.

Of them, vitamin E is preferable because no harmful effect is produced by excessive intake.

Examples of vitamin E that can be used include α-tocopherol, α-tocopherol acetate, α-tocopherol nicotinate, β-tocopherol, γ-tocopherol, δ-tocopherol and a mixture thereof.

Of them, α-tocopherol is preferable because it has various excellent physiological actions such as in-vivo antioxidative action, biomembrane stabilizing action and platelet aggregation suppressive action and a high oxidative stress suppressive effect.

Examples of the polyphenol include a flavonoid such as catechin, anthocyanin, tannin, rutin and isoflavone, a phenolic acid such as chlorogenic acid, ellagic acid, lignan, curcumin and coumarin.

<Amount of Lipid-Soluble Substance on Inner Surface of Hollow-Fiber Membrane>

In the hollow-fiber membrane in the embodiment, the amount of the lipid-soluble substance on the inner surface of the hollow-fiber membrane is 10 mg or more and 300 mg or less per $m^2$ of the inner surface of the hollow-fiber membrane.

If the amount of the lipid-soluble substance is 10 $mg/m^2$ or more, a hollow-fiber membrane blood purification device having stable antioxidative property can be obtained. In contrast, if the amount of the lipid-soluble substance is 300 $mg/m^2$ or less, a hollow-fiber membrane blood purification device having satisfactory blood compatibility can be produced at very reasonable manufacturing cost.

The amount of the lipid-soluble substance on the inner surface of the hollow-fiber membrane is preferably 10 $mg/m^2$ or more and 250 $mg/m^2$ or less and more preferably 10 $mg/m^2$ or more and 200 $mg/m^2$ or less.

Provided that the content of the lipid-soluble substance in the whole hollow-fiber membrane is 100 mass %, the amount of the lipid-soluble substance on the inner surface of the hollow-fiber membrane may be 40 to 95 mass %.

In the embodiment, the "amount of the lipid-soluble substance on the inner surface of the hollow-fiber membrane" refers to the content of the lipid-soluble substance (in terms of membrane area (1 $m^2$) of hollow-fiber membrane) attached, adsorbed or applied to the inner surface of the hollow-fiber membrane.

The amount of the lipid-soluble substance on the inner surface of the hollow-fiber membrane can be determined, for example, by the content of the lipid-soluble substance extracted by a solvent without destroying or dissolving the hollow-fiber membrane.

In the embodiment, the "inner surface of the hollow-fiber membrane" refers to the surface wall of the hollow portion of the hollow-fiber membrane.

In the embodiment, "the membrane area of the hollow-fiber membrane" refers to the effective total surface area of the hollow-fiber membrane involved in filtration or dialysis and more specifically to the inner surface area of the hollow-fiber membrane computationally obtained by multiplying the average inner diameter (diameter) of the hollow-fiber membrane, the circumference ratio, the number and effective length of the hollow-fiber membrane.

A method of determining the amount of the lipid-soluble substance on the inner surface of the hollow-fiber membrane will be described. First, a hollow-fiber membrane blood purification device is disassembled and a hollow-fiber membrane is taken out, washed with water and dried. Subsequently, to the dried hollow-fiber membrane weighed, an organic solvent dissolving a lipid-soluble substance or an aqueous surfactant solution, for example, a 75 v/v % aqueous ethanol solution or an aqueous polyethylene glycol-t-octylphenyl ether solution, is added and stirred to extract the lipid-soluble substance. Subsequently, liquid chromatography is carried out. Referring to a calibration curve obtained based on the peak area of a standard solution of a lipid-soluble substance, the concentration of the lipid-soluble substance in the extract is calculated. The value, which is computationally obtained from the concentration obtained above and the inner surface area of the hollow-fiber membrane used in extraction, provided that the extraction efficiency is 100%, is specified as the amount of the lipid-soluble substance ($mg/m^2$) on the inner surface of the hollow-fiber membrane.

<Container>

In the embodiment, the "container" refers to a case having a shape capable of housing a hollow-fiber membrane, for example, a cylindrical shape.

Examples of the material for the container include, but are not particularly limited to, a vinyl chloride resin, a polycarbonate resin, an ABS resin, an acrylic resin, a polyester resin, a polyolefin resin, a polysulfone resin, a polyphenylene oxide resin and a polyacetal resin. Generally, a polypropylene resin is used.

<Oxygen Transmission Rate of Container>

In the embodiment, the oxygen transmission rate of a container is $1.8\times10^{-10}$ $cm^3 \cdot cm/(cm^2 \cdot s \cdot cmHg)$ or less.

If the oxygen transmission rate is $1.8\times10^{-10}$ $cm^3 \cdot cm/(cm^2 \cdot s \cdot cmHg)$ or less, deterioration of the hollow-fiber membrane when sterilized with a radial ray can be prevented.

The oxygen transmission rate is preferably $1.5\times10^{-10}$ $cm^3 \cdot cm/(cm^2 \cdot s \cdot cmHg)$ or less, more preferably $1.4\times10^{-10}$ $cm^3 \cdot cm/(cm^2 \cdot s \cdot cmHg)$ or less and further preferably $1.3\times10^{-10}$ $cm^3 \cdot cm/(cm^2 \cdot s \cdot cmHg)$ or less.

In the embodiment, the oxygen transmission rate of a container can be determined by the isobaric method described in "JIS-K7126-2".

<Absorbance of the Body of Container at Wavelength 350 nm>

In the embodiment, the absorbance of the body of the container at a wavelength of 350 nm is preferably 0.35 or more and 2.00 or less.

If the absorbance is 0.35 or more, it is possible to prevent deterioration of the lipid-soluble substance by irradiation of light such as fluorescent light. If the absorbance is 2.00 or less, the state of a hollow-fiber membrane can be visually observed during medical treatment.

The absorbance is more preferably 0.50 or more and 1.50 or less and further preferably 0.50 or more and 1.00 or less.

In the embodiment, the body refers to the portion shown in FIG. 2. From the three sites (sites a, b, c in FIG. 3) of the body corresponding to separator lines, which divide the body almost equally into four parts in the longitudinal direction, pieces of about 1 cm squares are cut off and individual absorbance values (Abs) of the pieces from sites a, b and c at a wavelength of 350 nm are obtained by a spectrophotometer. The three values are averaged and regarded as the "absorbance of the body of the container at a wavelength of 350 nm".

If the thickness of the container, which is observed in the sectional view of the container cut in parallel to the circumferential direction, is not uniform, the separator lines (for dividing the body almost equally into four parts in the longitudinal direction) are drawn on the part of the container having the largest thickness.

<Hydrogen Peroxide Concentration in Initial Effluent (100 mL) when Saline is Passed Through>

In the embodiment, it is preferable that the hydrogen peroxide concentration in the initial effluent (100 mL) when saline is passed through is 10 ppm or less.

If the hydrogen peroxide concentration is high, the hollow-fiber membrane deteriorates. As a result, if the hollow-fiber membrane is used for blood treatment, the risk of releasing an eluted substance into the blood is high. During long-term use, a side effect and a complication will be caused. The hydrogen peroxide concentration in the initial effluent (100 mL) is preferably maintained at 10 ppm or less not only before shipping of a hollow-fiber membrane blood purification device but also when a package (bag) of the hollow-fiber membrane blood purification device is opened and used for treatment.

The hydrogen peroxide concentration is more preferably 9 ppm or less and further preferably 8 ppm or less.

In the embodiment, the hydrogen peroxide concentration can be measured by taking an aliquot of 100 mL from the effluent first discharged as the initial effluent, when saline is passed through the blood flow path of a hollow-fiber membrane blood purification device as a so-called priming treatment (including manual and automatic operations) and then subjecting the aliquot to the method described in Examples.

To obtain a hydrogen peroxide concentration of 10 ppm or less, it is preferable to previously measure the hydrogen peroxide concentrations of raw materials (e.g., a hydrophobic polymer, a hydrophilic polymer and a lipid-soluble substance, a solvent and individual solutions of these) for use in production of a hollow-fiber membrane and control the concentrations. For example, in the case of polyvinylpyrrolidone, if the hydrogen peroxide concentration of the raw material is 250 ppm or less, the hydrogen peroxide concentration in the initial effluent (100 mL) when saline is passed through can be controlled to fall within the range of 10 ppm or less, in the embodiment.

<Sterilizing Bag>

In the embodiment, the "sterilizing bag" refers to a bag having a shape capable of housing a hollow-fiber membrane blood purification device and keeping an aseptic condition therein.

Examples of the material for the sterilizing bag include, but are not particularly limited to, a film material such as polyethylene, poly(vinyl chloride), poly(vinylidene chloride), polyvinyl alcohol, polypropylene, polyester, polycarbonate, polystyrene, polyacrylonitrile, an ethylene-vinyl acetate copolymer, an ethylene-vinyl alcohol copolymer, an ethylene-methacrylic acid copolymer, nylon and cellophane; an aluminum foil; an aluminum-deposited film; and an inorganic oxide deposited film such as silica and alumina. Alternatively, a composite material formed of these films and permeating neither oxygen gas nor steam, may be used.

The composite material is preferably constituted of a film material having sealing property and an impermeable material. Of them, a film using an aluminum foil efficiently blocking oxygen gas and steam as a constituent layer, more specifically, a laminate sheet constituted of a polyester film as the outer layer, aluminum foil as an intermediate layer and a polyethylene film as the inner layer and having both functions, i.e., impermeability and heat sealing property, is preferably used.

A container is preferably housed in a sterilizing bag by using a sealing method, such as a heat sealing method, an impulse sealing method, a meltdown sealing method, a frame sealing method, an ultrasonic sealing method and a high frequency sealing method.

Although situation varies depending upon the sterilization method, if not only a container but also an oxygen gas/steam-impermeable package (bag) is employed, even if a storage period is relatively long, it is possible to keep a hollow-fiber membrane blood purification device such that the hydrogen peroxide concentration of the initial effluent falls in the range of 10 ppm or less.

<Oxygen Transmission Rate of Sterilizing Bag>

The oxygen transmission rate of a sterilizing bag is preferably $1.5 \times 10^{-10}$ cm$^3$·cm/(cm$^2$·s·cmHg) or less, more preferably $1.45 \times 10^{-10}$ cm$^3$·cm/(cm$^2$·s·cmHg) or less and further preferably $1.4 \times 10^{-10}$ cm$^3$·cm/(cm$^2$·s·cmHg) or less.

If the oxygen transmission rate is $1.5 \times 10^{-10}$ cm$^3$·cm/(cm$^2$·s·cmHg) or less, deterioration of the hollow-fiber membrane by radiation sterilization can be prevented.

In the embodiment, the oxygen transmission rate of a sterilizing bag can be determined by the isobaric method described in "JIS-K7126-2".

<Method for Producing Hollow-Fiber Membrane>

In the method for producing a hollow-fiber membrane according to the embodiment, a conventional membrane production step using a spinning dope for membrane production at least containing a hydrophobic polymer and a hydrophilic polymer is carried out.

The spinning dope for membrane production can be prepared by dissolving a hydrophobic polymer and a hydrophilic polymer in a solvent.

Examples of the solvent include dimethylacetamide, dimethylsulfoxide, N-methyl-2-pyrrolidone, dimethylformamide, sulfolane and dioxane.

These solvents may be used alone or in combination of two or more as a solvent mixture.

The concentration of the hydrophobic polymer in a spinning dope for membrane production is not particularly limited as long as a membrane can be produced and the obtained hollow-fiber membrane can serve as a permeable membrane. The concentration is preferably 5 mass % or more and 50 mass % or less and more preferably 10 mass % or more and 40 mass % or less. The concentration of the hydrophobic polymer in a spinning dope for membrane production is further preferably 10 mass % or more and 35 mass % or less because the lower the concentration of the hydrophobic polymer, the higher water-permeability can be attained.

The concentration of the hydrophilic polymer in a spinning dope for membrane production is controlled such that the mixing ratio of a hydrophilic polymer relative to a hydrophobic polymer falls within the range of preferably 30 mass % or less and more preferably 5 mass % or more and 30 mass % or less, further preferably 10 mass % or more and 30 mass % or less.

If the mixing ratio of a hydrophilic polymer relative to a hydrophobic polymer is 30 mass % or less, the elution amount of hydrophilic polymer can be suppressed. The mixing ratio of a hydrophilic polymer relative to a hydrophobic polymer is preferably 10 mass % or more. If so, the concentration of a hydrophilic polymer on the functional surface of a separation membrane can be controlled within a preferred range; the effect of suppressing protein adsorption can be increased; and excellent blood compatibility can be provided.

The membrane production step is not particularly limited. First of all, a tube-in-orifice spinneret is used. A spinning dope for membrane production is allowed to discharge from the orifice of the spinneret simultaneously with a hollow-portion internal liquid for coagulating the spinning dope for membrane production from the tube, in the air.

As the hollow-portion internal liquid, water or a water-based liquid can be used. A mixed solution of a solvent used in the spinning dope for membrane production and water is preferably used in general.

As the hollow-portion internal liquid, for example, 20 mass % or more and a 70 mass % or less aqueous dimethylacetamide solution can be mentioned.

If the discharge rate of the spinning dope for membrane production and the discharge rate of the hollow-portion internal liquid are controlled, the inner diameter and thickness of the hollow-fiber membrane can be controlled to be desired values.

The inner diameter of the hollow-fiber membrane for use in blood treatment is, in general, satisfactorily 170 μm or more and 250 μm or less and preferably 180 μm or more and 220 μm or less.

The thickness of the hollow-fiber membrane is preferably 50 μm or less in view of efficiency of a permeable membrane in removing low molecular-weight substances by diffusion due to mass transfer resistance, and preferably 10 μm or more in view of strength.

The spinning dope for membrane production discharged together with the hollow-portion internal liquid from a spinneret is allowed to flow through an air gap, introduced in a coagulation bath consisting mainly of water and provided under the spinneret, and allowed to soak for a predetermined time until coagulation is completed.

The air gap refers to the space between the spinneret and the coagulation bath. The spinning dope for membrane production is coagulated from the side to be the inner surface by a poor solvent component such as water in the hollow-portion internal liquid simultaneously discharged from the spinneret.

To form a smooth hollow-fiber membrane surface and obtain a stable hollow-fiber membrane structure, a draft at the initiation of coagulation is preferably 1 or less and more preferably 0.95 or less. The draft herein refers to the ratio of the linear velocity of the spinning dope for membrane production discharged and the take-over speed.

Then, the residual solvent on the hollow-fiber membrane is removed by washing with e.g., hot water and a wet-state hollow-fiber membrane is directly wound up. A bundle of the hollow-fiber membrane is prepared by controlling length and number so as to provide a desired membrane area, wrapped with the film formed of e.g., polyethylene, placed in a drying room and dried by introducing superheated steam into the drying room.

Washing is preferably carried out with hot water of 60° C. or more for 120 seconds or more in order to remove not only a solvent but also an unnecessary hydrophilic polymer, and more preferably with hot water of 70° C. or more for 150 seconds or more.

The superheated steam may be introduced into a drying room under normal pressure or following reducing a pressure in a drying room. In order to reduce drying time and suppress thermal decomposition, it is preferred to introduce steam having the inversion temperature (the point at which the evaporation rate becomes constant regardless of humidity) or more and 200° C. or less.

<Step of Assembling Hollow-Fiber Membrane Blood Purification Device>

A hollow-fiber membrane blood purification device is assembled by using the hollow-fiber membrane obtained by the method for producing a hollow-fiber membrane.

A container is filled with a hollow-fiber membrane. For example, a cylindrical container having two nozzles at the side surface near both ends is filled with a hollow-fiber membrane. Then, the both ends each are embedded in a urethane resin. Next, the cured urethane part is cut and processed to form the edge at which the hollow-fiber membrane is exposed. The both ends each are closed with a header cap having a nozzle for input (output) of a liquid such as blood and dialyzing fluid. In this manner, a blood purification device is assembled.

<Step of Immobilizing Lipid-Soluble Substance>

As a method of immobilizing a lipid-soluble substance onto the surface of a hollow-fiber membrane, basically, a conventional method can be used.

Examples of the method of immobilizing a lipid-soluble substance onto the surface of a hollow-fiber membrane include a method of allowing a lipid-soluble substance to be present in the entire hollow-fiber membrane by adding the lipid-soluble substance to a spinning dope for membrane production when a membrane is produced (for example, Japanese Patent Laid-Open No. 9-66225); a method of allowing a lipid-soluble substance to be present on the surface of the hollow-fiber membrane by adding the lipid-soluble substance and, if necessary, a surfactant, to a hollow-portion internal liquid (for example, Japanese Patent No. 4038583); and a method (coating method) of supplying a solution of a lipid-soluble substance into the hollow portion of a hollow-fiber membrane to deposit the lipid-soluble substance onto the surface of the hollow-fiber membrane (for example, Japanese Patent Laid-Open No. 2006-296931). As the addition (immobilization) method, any method other than the aforementioned conventional methods may be used.

Of them, the coating method can realize production of hollow-fiber membranes different in permeability by using existing equipment and product lineup.

In the methods of adding the lipid-soluble substance to a spinning dope for membrane production and a hollow-portion internal liquid, a lipid-soluble substance is immobilized to a hollow-fiber membrane when the hollow-fiber membrane is produced by spinning.

In the case of the coating method, a lipid-soluble substance is immobilized on a hollow-fiber membrane, and then, a blood purification device may be assembled by using the hollow-fiber membrane. Alternatively, the lipid-soluble substance may be immobilized after a blood purification device is assembled or during the middle of the assembling step, by passing a coating liquid through the device.

In the embodiment, to control the amount of the lipid-soluble substance on the inner surface of the hollow-fiber membrane to be 10 mg/m$^2$ or more and 300 mg/m$^2$ or less, for example, in the coating method, the concentration of the lipid-soluble substance in a coating liquid is controlled to be preferably 0.1 mass % or more and 30 mass % or less, more preferably 0.1 mass % or more and 20 mass % or less and further preferably 0.1 mass % or more and 10 mass % or less.

<Sterilization Step for Hollow-Fiber Membrane Blood Purification Device>

A hollow-fiber membrane blood purification device is subjected to a radiation sterilization step. In radiation sterilization, e.g., an electron beam, γ ray and X ray can be used. The irradiation dose of a radial ray such as a γ ray and an electron beam is preferably 5 kGy or more and 50 kGy or less and more preferably 20 kGy or more 40 kGy or less.

<Oxygen Concentration in Container During Sterilization>

A hollow-fiber membrane blood purification device is preferably sterilized with a radial ray in a container having an oxygen concentration of 10% or less, preferably 8% or less and more preferably 5% or less.

Radiation sterilization plays two roles: sterilization, which is an essential treatment for manufacturing a medical device, and a treatment for insolubilizing a hydrophilic polymer by crosslinking. If the oxygen concentration is 10% or less, oxidative decomposition of a membrane material is suppressed from proceeding and elution from a hollow-fiber membrane can be reduced.

If radiation sterilization is carried out by controlling the oxygen concentration within a container to be 10% or less, it is easy to keep a hollow-fiber membrane blood purification device such that the hydrogen peroxide concentration in the initial effluent falls within the range of 10 ppm or less, although situation varies depending upon the length of a storage period.

How to control the oxygen concentration within a container to be 10% or less will be described below.

<Replacement with Inert Gas>

After an enclosed space such as a glove box is filled with an inert gas, the hollow-fiber membrane blood purification device is placed. After the air within the hollow-fiber membrane blood purification device is replaced with the inert gas, the hollow-fiber membrane blood purification device is closed airtight by a stopper or placed in a sterilizing bag having an oxygen transmission rate of $1.5 \times 10^{-10}$ cm$^3$·cm/(cm$^2$·s·cmHg) or less. The inert gas refers to an unreactive gas such as carbon dioxide, nitrogen, argon and helium.

<Introduction of Oxygen Scavenger>

A hollow-fiber membrane blood purification device is put in a package (bag) (sterilizing bag may be used) together with an oxygen scavenger and allowed to leave for a predetermined time to remove oxygen in the package (bag). Since oxygen is selectively removed from the air in the package (bag) by the oxygen scavenger, the atmosphere of the hollow-fiber membrane blood purification device consists of the inert gas.

Although situation varies depending upon the type of oxygen scavenger to be used and the size of a package (bag), the oxygen concentration in a package (bag) reaches 0.1% or less generally by leaving the package (bag) for about 48 hours after an oxygen scavenger is put in the package (bag) and closed airtight.

Examples of the oxygen scavenger include sulfite, bisulfite, dithionite, hydroquinone, catechol, resorcin, pyrogallol, gallic acid, rongalite, ascorbic acid and salts of these, sorbose, glucose, lignin, dibutylhydroxytoluene, dibutylhydroxyanisole and a metal powder such as iron powder including a ferrous salt.

These can be used alone or in combination of two or more as the oxygen scavenger.

To an oxygen scavenger containing a metal powder as a main ingredient, if necessary, an oxidation catalyst such as a halogen metal compound may be added. Examples of the oxidation catalyst include sodium chloride, potassium chloride, magnesium chloride, calcium chloride, aluminum chloride, ferrous chloride, ferric chloride, sodium bromide, potassium bromide, magnesium bromide, calcium bromide, iron bromide, nickel bromide, sodium iodide, potassium iodide, magnesium iodide, calcium iodide and iron iodide.

These can be used alone or in combination of two or more as an oxidation catalyst.

A method of providing a water releasing function, for example, a method of enclosing a device together with a moisture releasing oxygen scavenger (for example, AGELESS (registered trademark) Z-200PT, manufactured by Mitsubishi Gas Chemical Company, Inc.) or a porous carrier, such as a zeolite powder impregnated with water is mentioned.

Examples of the shape of an oxygen scavenger include, but are not particularly limited to, powdery, granular, clumpy and sheet. Alternatively, a sheet or film like oxygen scavenger formed of a thermoplastic resin having an oxygen absorbent composition dispersed therein.

A deodorant, a refresher and a functional filler other than these may be added.

<Reducing Pressure within Sterilizing Bag>

After a hollow-fiber membrane blood purification device is disposed in a sterilizing bag, the sterilizing bag is deaerated by a degasser and zipped. It is not necessary to deaerate the container up to a vacuum but satisfactory up to an oxygen concentration of about 10% or less and preferably up to a lower oxygen concentration.

<Moisturization of Hollow-Fiber Membrane or Introduction of Filling Fluid>

Before the hollow-fiber membrane blood purification device having a lipid-soluble substance immobilized is sterilized, the hollow-fiber membrane may be moistened with an aqueous solution. If a hollow-fiber membrane is moistened with an aqueous solution, the hollow-fiber membrane is stabilized and rarely changed in properties including water-permeability, dialyzability and filterability. Examples of the method of moisturizing the hollow-fiber membrane with an aqueous solution include a method of filling a container filled with a hollow-fiber membrane, with an aqueous solution and a method of filling a container with an aqueous solution and then removing the solution.

In the moisturizing step of a hollow-fiber membrane, a step of adding a sterilization protective agent (described later) can be simultaneously carried out.

<Coating with Barrier Material>

A container or a sterilizing bag is coated with a barrier material having a low oxygen transmission rate. The barrier material can be obtained by e.g., spraying or dipping. Examples of the barrier material include poly(vinyl chloride), poly(ethylene terephthalate), nylon, poly(vinylidene chloride), an ethylene-vinyl alcohol copolymer, a vinylidene chloride-methyl acrylate copolymer, alumina, silica and nanocomposite. Derivatives and complexes of these can be also used.

These can be used alone or in combination of two or more as a barrier material. Furthermore, a plurality of coating layers may be formed by applying a barrier material.

<Step of Adding a Sterilization Protective Agent>

The sterilization protective agent is used for protecting a hydrophilic polymer of a hollow-fiber membrane so as not to significantly degenerate by radiation energy applied in the sterilization step. In other words, the sterilization protective agent is a radical scavenger having a plurality of hydroxyl groups and aromatic rings in a molecule.

Examples of the sterilization protective agent include a (polyhydric) alcohol such as glycerin and propylene glycol; a water-soluble sugar such as an oligosaccharide and a polysaccharide; and an inorganic salt having an antioxidant activity such as a sulfite.

These can be used alone or in combination of two or more, as the sterilization protective agent.

As a method of impregnating a hollow-fiber membrane with a sterilization protective agent, a method involving dissolving a sterilization protective agent in an appropriate solvent and introducing the solution in a hollow-fiber membrane blood purification device, more specifically, a method involvinv dissolving a sterilization protective agent in water or saline and filling the inner space of a hollow-fiber membrane blood purification device with the resultant solution, or impregnating only a hollow-fiber membrane with the solution, is mentioned. In the moisturizing step, an aqueous solution containing a sterilization protective agent may be used as an aqueous solution for moisturization.

If a sterilization protective agent is present in a hollow-fiber membrane blood purification device, the hollow-fiber membrane blood purification device, in particular, a hollow-fiber membrane, can be suppressed from degenerating by a radiation sterilization treatment.

When a sterilization protective agent is used as a solution, the concentration of the sterilization protective agent may be determined so as to be optimal depending upon the material for a hollow-fiber membrane blood purification device, the type of hydrophilic polymer and the conditions of sterilization. The concentration is preferably 0.001 mass % or more and 1 mass % or less and more preferably 0.005 mass % or more and 0.5 mass % or less.

EXAMPLES

The present invention will be more specifically described by way of Examples; however, the present invention is not limited by these Examples. The measuring methods used in Examples are as follows.

<Method for Measuring the Amount of the Lipid-Soluble Substance on the Inner Surface of the Hollow-Fiber Membrane>

A hollow-fiber membrane blood purification device was disassembled and a hollow-fiber membrane was taken out, washed with water and dried.

Subsequently, the dried hollow-fiber membrane (4 g) was weighed in a glass bottle, a 75 v/v % aqueous ethanol solution (80 mL) was added thereto and then a lipid-soluble substance was extracted while applying ultrasonic vibration at room temperature for 60 minutes.

Quantification operation was carried out by liquid chromatography using the following apparatus. Based on a calibration curve obtained from a peak area when a lipid-soluble substance standard solution is used, the amount of the lipid-soluble substance in the extract was obtained.

A high performance liquid chromatography system (pump: JASCO PU-1580, detector: Shimadzu RID-6A, Autoinjector: Shimadzu SIL-6B, Data processing: Tohso GPC-8020, column oven: GL Sciences 556) was equipped with a column (ODP-506E packed column for H-PLC, manufactured by Shodex Asahipak). Methanol for high performance liquid chromatography serving as a mobile phase was passed through the column at a flow rate of 1 mL/min at a column temperature of 40° C. From the area of an ultraviolet absorption peak, the concentration of a lipid-soluble substance was obtained. Based on the lipid-soluble substance concentration, the amount of the lipid-soluble substance on the inner surface of the hollow-fiber membrane ($mg/m^2$) was obtained, provided that the extraction efficiency was 100%.

<Method for Measuring Oxygen Transmission Rate of Container>

The oxygen transmission rate of a container was determined by the isobaric method described in "JIS-K7126-2".

<Method of Measuring Absorbance of the Body of the Container at a Wavelength of 350 nm>

From the three sites (sites a, b, c in FIG. 3) of the body of the container corresponding to separator lines, which divide the body almost equally into four parts in the longitudinal direction, pieces of about 1 cm squares were cut off, and individual absorbance values (Abs) of the pieces from sites a, b and c at a wavelength of 350 nm were obtained by a spectrophotometer (V-650, manufactured by JASCO Corporation) and averaged.

<Method for Determining the Oxygen Transmission Rate of a Sterilizing Bag>

The oxygen transmission rate of a sterilizing bag was determined by the isobaric method described in "JIS-K7126-2".

<Method for Measuring the Concentrations of Oxygen in a Container and a Sterilizing Bag>

Oxygen concentration was measured by directly sticking the needle of an oxygen meter (RO-103, manufactured by Iijima Electronics Corporation) to the rubber part of a hollow-fiber membrane blood purification device closed airtight by a stopper, for example, the rubber part at the center of the stopper. The oxygen concentration of a sterilizing bag was measured by directly inserting the needle of an oxygen meter (RO-103, manufactured by Iijima Electronics Corporation) in a sterilizing bag of a hollow-fiber membrane blood purification device.

<Method of Measuring Hydrogen Peroxide Concentration>

Saline was allowed to flow through the blood flow path of a hollow-fiber membrane blood purification device at a flow rate of 200 mL/minute and the first effluent (100 mL) was sampled. From the effluent, a sample of 3 mL was taken and colored by use of Pack Test, WAK-H2O2 (manufactured by Kyoritsu Chemical-Check Lab. Corp.). Thereafter, the concentration of hydrogen peroxide was measured by use of Digital Pack Test (manufactured by Kyoritsu Chemical-Check Lab. Corp.).

<Measurement of Lactate Dehydrogenase (LDH) Activity>

A hollow-fiber membrane blood purification device was disassembled, a hollow-fiber membrane was taken out. The hollow-fiber membrane was adhered with an epoxy adhesive at both ends so as to obtain an effective length of 15 cm and an inner surface area of the hollow-fiber membrane of 50 $mm^2$ to prepare a mini blood purification device. To the mini blood purification device, 3 mL of saline (OTSUKA NORMAL SALINE, Otsuka Pharmaceutical Co., Ltd.) was supplied and allowed to flow at a flow rate 0.6 mL/min into a hollow portion of the hollow-fiber membrane for washing.

Thereafter, heparin-added human blood (15 mL) was warmed to a temperature of 37° C. and circulated in the mini blood purification device at a flow rate of 1.2 mL/min for 4 hours. After the circulation, the hollow portion and the exterior of the mini blood purification device each were washed with 10 mL of saline.

A hollow-fiber membrane was taken out from the mini blood purification device washed, shredded and put in a Spitz tube for measurement of LDH activity, which was used as a sample for LDH activity measurement.

Next, TritonX-100 (Nacalai Tesque Inc.) was dissolved in a phosphate buffer solution (PBS) (Wako Pure Chemical Industries Ltd.) to obtain a 0.5 vol % TritonX-100/PBS solution. This solution (0.5 mL) was added to the Spitz tube for LDH activity measurement, centrifuged (at 2700 rpm×5 min) to sink the hollow-fiber membrane in the solution. Extraction was carried out while shaking for 60 minutes to destroy cells (principally platelets) attached to the hollow-fiber membrane. In this manner LDH in the cells was extracted. From the extract, an aliquot (0.05 mL) was taken. To this, further a 0.6 mM sodium pyruvate solution (2.7 mL) and a 1.277 mg/mL nicotinamide adenine dinucleotide (NADH) solution (0.3 mL) were added and reacted. The reaction was further carried out at 37° C. for one hour. The absorbance of the reaction solution at 340 nm was measured.

Similarly, the absorbance was measured with respect to the hollow-fiber membrane (blank) which was not reacted with blood. The difference in absorbance was calculated in accordance with the calculation expression (1). The value obtained by the calculation expression (1) was divided by the inner surface area of the hollow-fiber membrane, in other words, the value obtained in accordance with calculation expression (2) was determined as LDH activity.

$$\Delta 340 \text{ nm} = \text{absorbance of sample after 60 minutes} - \text{absorbance of blank after 60 minutes} \quad (1)$$

$$\text{LDH activity} = \Delta 340 \text{ nm/the inner surface area of the hollow-fiber membrane} \quad (2)$$

It was evaluated that the larger the value obtained by the above expression (2), the larger the amount of platelets attached to the inner surface of the hollow-fiber membrane. The LDH activity of a hollow-fiber membrane blood purification device was evaluated as follows.

LDH activity is 10 ($\Delta$abs/hr·m$^2$) or less . . . ⊚

LDH activity is larger than 10 ($\Delta$abs/hr·m$^2$) and 50 ($\Delta$abs/hr·m$^2$) or less . . . ○

LDH activity is larger than 50 ($\Delta$abs/hr·m$^2$) . . . x

<Measurement of Antioxidant Capacity>

Ferric chloride hexahydrate was dissolved in pure water to prepare a 0.3 w/v % aqueous solution thereof (amount (g) of solute in the solution (100 mL)). A hollow-fiber membrane blood purification device was disassembled and a hollow-fiber membrane was taken out, washed with water and dried under vacuum at 40° C. The hollow-fiber membrane (1 g) dried and an aqueous ferric chloride solution (20 mL) were weighed in a glass bottle, defoamed at 60 mmHg for 10 minutes, incubated while shaking at 30° C. for 4 hours (iron (iii) ion was reduced by a lipid-soluble vitamin present on the surface of the hollow-fiber membrane and converted into iron (ii)). The aqueous solution (2.6 mL) incubated, ethanol (0.7 mL) and a 0.5 w/v % aqueous 2,2'-dipyridyl ethanol solution (0.7 mL) separately prepared were mixed and incubated while shaking at 30° C. for 30 minutes (iron (ii) and bipyridyl formed a complex and produced color).

The absorbance of the colored solution was measured at 520 nm by a spectrometer. In place of the hollow-fiber membrane, an ethanol solution of a lipid-soluble vitamin known in concentration was subjected to the same operation including incubation, a color reaction and measurement of absorbance to prepare a calibration curve. Based on the calibration curve, the antioxidant capacity exhibited by the hollow-fiber membrane (1 g) was obtained in terms of weight of the lipid-soluble vitamin.

The antioxidant capacity was evaluated in terms of the weight of the lipid-soluble vitamin per the inner surface of the hollow-fiber membrane (1 m$^2$), as follows.

Antioxidant capacity is larger than 15 (mg/m$^2$) . . . ○

Antioxidant capacity is 15 (mg/m$^2$) or less . . . x

<Measurement of Antioxidant Capacity when Exposed to Fluorescent Light>

A hollow-fiber membrane blood purification device was exposed to a fluorescent lamp (Type 40, FLR40S-N/M-X.36, manufactured by Panasonic Corporation) for 300 hours. The distance between the fluorescent lamp and the surface of blood purification device was 120 cm and illuminance was 500 (1x) (luminometer: LUX Hi TESTER3421, manufactured by HIOKI). The hollow-fiber membrane exposed to light was taken out, washed with water and dried at 40° C. under vacuum. The hollow-fiber membrane (1 g) dried and a 0.3 w/v % aqueous ferric chloride solution (20 mL) were weighed in a glass bottle, defoamed at 60 mmHg for 10 minutes and incubated while shaking at 30° C. for 4 hours (iron (iii) ion was reduced by a lipid-soluble vitamin present on the surface of the hollow-fiber membrane and converted into iron (ii)). The aqueous solution (2.6 mL) incubated, ethanol (0.7 mL) and a 0.5 w/v % aqueous 2,2'-dipyridyl ethanol solution (0.7 mL) separately prepared were mixed and incubated while shaking at 30° C. for 30 minutes (iron (ii) and bipyridyl formed a complex and produced color).

The absorbance of the colored solution was measured at 520 nm by a spectrometer. In place of the hollow-fiber membrane, an ethanol solution of a lipid-soluble vitamin known in concentration was subjected to the same operation including incubation, a color reaction and measurement of absorbance to prepare a calibration curve. Based on the calibration curve, the antioxidant capacity exhibited by the hollow-fiber membrane (1 g) was obtained in terms of weight of the lipid-soluble vitamin.

The antioxidant capacity when exposed to fluorescent light was evaluated as follows.

The antioxidant capacity when exposed to fluorescent light is larger than 15 (mg/m$^2$) . . . ○

The antioxidant capacity when exposed to fluorescent light is 15 (mg/m$^2$) or less . . . x Example 1

As a spinning dope for membrane production, polysulfone (SOLVAY SPECIALTY POLYMERS, P-1700, solubility parameter δ 9.90)(17.5 mass %) and polyvinylpyrrolidone (BASF K90)(3.5 mass %) were dissolved in N,N-dimethylacetamide (79.0 mass %) to prepare a homogeneous solution. The mixing ratio of polyvinylpyrrolidone to polysulfone in the spinning dope for membrane production was 17 mass %. The obtained spinning dope for membrane production, which was kept at 60° C., and a hollow-portion internal liquid consisting of a solution mixture of N,N-dimethylacetamide (58.1 mass %) and water (41.9 mass %), were simultaneously discharged from a double annular spinneret, passed through an air gap of 0.96 m, soaked in a coagulation bath containing (hot) water of 75° C., and wound up at a rate of 80 m/minute. The yarn bundle wound up was cut and washed by spraying hot water of 80° C. with a shower over the cut surface of the yarn bundle for two hours to remove residual solvent in the membrane. The membrane was further put in a drying room and dried by introducing superheated steam of 180° C. to obtain a dried membrane having a moisture content of less than 1%.

The discharge amounts of spinning dope for membrane production and hollow-portion internal liquid were controlled so as to obtain a dried membrane having a thickness of 35 μm and an inner diameter of 185 μm.

A hollow-fiber membrane bundle was prepared so as to provide an effective membrane area of 1.5 m$^2$ when the dried membranes were integrated into a blood purification device, and then packaged in a polyethylene (PE) film, and filled in a polypropylene cylindrical container (thickness 2.1 mm) having inlet and outlet nozzles for a liquid and an oxygen transmission rate of $1.3 \times 10^{-10}$ cm$^3$·cm/(cm$^2$·s·cmHg). The both ends thereof each were embedded in a urethane resin and the cured urethane part was cut and processed to obtain the edge at which the hollow-fiber membrane was exposed. The both ends each were closed with a header cap having a blood inlet (outlet) nozzle. In this manner, a blood purification device having an inner surface area of the hollow-fiber membrane of 1.5 m² was assembled.

In a 57 mass % aqueous isopropanol solution, α-tocopherol (special grade, Wako Pure Chemical Industries Ltd.) was dissolved to prepare a 0.54 mass % coating liquid. This solution was supplied from a blood inlet nozzle of a blood purification device at 24° C. to the inner surface of the hollow-fiber membrane for one minute to bring α-tocopherol into contact with the inner surface. Thereafter, air was flashed to remove residual liquid in the hollow portion. Then, dry air, i.e., an isopropanol atmosphere of 24° C., was supplied for 30 minutes to dry and remove the solvent. In this manner, α-tocopherol was immobilized.

A nitrogen substitution step was carried out in a glove box filled with nitrogen to replace the atmosphere in the blood purification device with nitrogen and all nozzles were closed airtight.

The oxygen concentration within the container, which was measured 20 days after replacement with nitrogen, was 8%. Immediately after that, the blood purification device was sterilized with a γ ray at a dose of 25 kGy.

Example 2

The same method as in Example 1 was carried out except that a polycarbonate cylindrical container (thickness: 2.0 mm) having an oxygen transmission rate of $1.1 \times 10^{-10}$ cm³·cm/(cm²·s·cmHg) was filled with a hollow-fiber membrane bundle and that a 3.21 mass % aqueous solution of α-tocopherol (special glade, by Wako Pure Chemical Industries Ltd.) in 57 mass % isopropanol was used as a coating liquid.

The oxygen concentration within the container, which was measured 20 days after replacement with nitrogen, was 5%.

Example 3

The same method as in Example 1 was carried out except that a blood purification device was enclosed in a sterilizing bag NP-5 (oxygen transmission rate: $1.5 \times 10^{-15}$ cm⁻³·cm/(cm²·s·cmHg), thickness: 0.78 μm) manufactured by ASAHIKASEI PAX CORPORATION.

The oxygen concentration within the container, which was measured 20 days after replacement with nitrogen, was 2%.

Example 4

The same method as in Example 1 was carried out except that a polyethylene terephthalate cylindrical container (thickness: 2.1 mm) having an oxygen transmission rate of $1.5 \times 10^{-10}$ cm³·cm/(cm²·s·cmHg) was filled with a hollow-fiber membrane bundle, and that 0.11 mass % aqueous solution of α-tocopherol (special glade, Wako Pure Chemical Industries Ltd.) in 57 mass % isopropanol was used as a coating liquid.

The oxygen concentration within the container, which was measured 20 days after replacement with nitrogen, was 10%.

Example 5

The same method as in Example 1 was carried out except that a moisturizing step was carried out in place of a replacement step with nitrogen by filling a blood flow path and a filtrate flow path of a blood purification device with an aqueous solution containing 0.06 mass % sodium pyrosulfite as a sterilization protective agent and 0.03 mass % sodium carbonate as a pH adjuster, and that all nozzles were closed airtight.

The oxygen concentration within the container, which was measured 20 days after replacement with nitrogen, was 1% or less.

Example 6

The same method as in Example 1 was carried out except that the oxygen concentration within the container was measured one day after replacement with nitrogen.

The oxygen concentration within the container, which was measured one day after replacement with nitrogen, was 1%.

Example 7

As a spinning dope for membrane production, polyethersulfone (4800 P, SUMITOMO CHEMICAL Co., Ltd.)(17.5 mass %), polyvinylpyrrolidone (K90, BASF)(3.5 mass %), triethylene glycol (TEG) (Mitsubishi Chemical Corporation) (31.2 mass %) and water (1.0 mass %) were dissolved in N,N-dimethylacetamide (46.8 mass %) to prepare a homogeneous solution. The mixing ratio of polyvinylpyrrolidone to polyethersulfone in the spinning dope for membrane production was 20 mass %. The obtained spinning dope for membrane production, which was kept at 45° C., and a hollow-portion internal liquid, i.e., water, were simultaneously discharged from a double annular spinneret, passed through an air gap of 600 mm, soaked in a coagulation bath (DMAc:TEG:water=6:4:90) of 70° C., and wound up at a rate of 60 m/minute. The yarn bundle wound up was cut and washed by spraying hot water of 80° C. with a shower over the cut surface of the yarn bundle for two hours to remove residual solvent in the membrane. The membrane was further put in a drying room and dried by introducing superheated steam of 180° C. to obtain a dried membrane having a moisture content of less than 1%.

The discharge amounts of spinning dope for membrane production and hollow-portion internal liquid were controlled so as to obtain a dried membrane having a thickness of 35 μm and an inner diameter of 185 μm.

The resultant dried membrane was subjected to the same method as in Example 1.

The oxygen concentration within the container, which was measured 20 days after replacement with nitrogen, was 9%.

Example 8

As a spinning dope for membrane production, cellulose triacetate (Daicel Chemical) (16.0 mass %), an ethylene-vinyl alcohol polymer (EVAL EC-F100A, Kuraray Co., Ltd.)(3 mass %) having a saponification degree of 99% and triethylene glycol (Mitsui Chemicals, Inc.)(24.3 mass %) were dissolved in N-methyl-2-pyrrolidone (Mitsubishi Chemical Corporation) (56.7 mass %) at 145° C. to prepare a homogeneous solution. The mixing ratio of the ethylene-vinyl alcohol polymer to cellulose triacetate in the spinning dope for membrane production was 16%. The obtained spinning dope for membrane production, which was kept at 120° C. was discharged from a double annular spinneret; at the same time, air was supplied to form a hollow. The hollow-fiber form spinning dope was discharged from the double annular spinneret, allowed to fly in the air in a distance of 300 mm, soaked in a coagulation bath containing (hot) water of 70° C. and wound up at a rate of 80 m/minute. The yarn bundle wound up was cut and washed by spraying hot water of 80° C. with a shower over the cut surface of the yarn bundle for two hours to remove residual solvent in the membrane. The membrane was further put in a drying room and dried by introducing superheated steam of 180° C. to obtain a dried membrane having a moisture content of less than 1%.

The discharge amounts of spinning dope for membrane production and hollow-portion internal liquid were controlled so as to obtain a dried membrane having a thickness of 35 μm and an inner diameter of 185 μm.

A hollow-fiber membrane bundle was prepared so as to provide an inner membrane area of the hollow-fiber membrane of 1.5 m² when the dried membranes were integrated into a blood purification device, and then packaged in a polyethylene (PE) film, and filled in a polypropylene cylindrical container (thickness 2.2 mm) having inlet and outlet nozzles for a liquid and an oxygen transmission rate of $1.3 \times 10^{-10}$ cm³·cm/(cm²·s·cmHg). The both ends thereof each were embedded in a urethane resin and the cured urethane part was cut and processed to obtain an edge at which hollow-fiber membranes were exposed. The both ends each were closed with a header cap having a blood inlet (outlet) nozzle. In this manner, a blood purification device was assembled.

A coating liquid containing 65 mass % of glycerin, acetone (34.45 mass %) and α-tocopherol (special grade, Wako Pure Chemical Industries Ltd.)(0.55 mass %) was supplied from a blood inlet nozzle of a blood purification device at 24° C. toward the inner surface of the hollow-fiber membrane for one minute to bring α-tocopherol into contact with the inner surface. Thereafter, air was flashed to remove residual liquid in the hollow portion. Then, dry air, i.e., an isopropanol atmosphere, of 24° C. was supplied for 30 minutes to dry and remove the solvent to immobilize α-tocopherol.

As a moisturizing step, an aqueous solution containing sodium pyrosulfite (0.06 mass %) as a sterilization protective agent and sodium carbonate (0.03 mass %) as a pH adjuster was supplied to a blood flow path and a filtrate flow path of the blood purification device and all nozzles were closed airtight.

The oxygen concentration in the container, which was measured 20 days after moisturization, was 1% or less. Immediately after that, the blood purification device was sterilized with a γ ray at a dose of 25 kGy.

Example 9

The same method as in Example 1 was carried out except that a polypropylene cylindrical container (thickness: 1.2 mm) having an oxygen transmission rate of $1.8 \times 10^{-10}$ cm³·cm/(cm²·s·cmHg) was filled with a hollow-fiber membrane bundle.

The oxygen concentration within the container, which was measured 20 days after replacement with nitrogen, was 10%.

Example 10

The same method as in Example 1 was carried out except that a polypropylene cylindrical container (thickness: 3.3 mm) having an oxygen transmission rate of $1.0 \times 10^{-10}$ cm³·cm/(cm²·s·cmHg) was filled with a hollow-fiber membrane bundle.

The oxygen concentration within the container, which was measured 20 days after replacement with nitrogen, was 6%.

Comparative Example 1

The same method as in Example 1 was carried out except that a coating liquid prepared by dissolving α-tocopherol (special grade, Wako Pure Chemical Industries Ltd.) (3.75 mass %) in a 57 mass % aqueous solution of isopropanol was used.

The oxygen concentration within the container, which was measured 20 days after replacement with nitrogen, was 8%.

Comparative Example 2

The same method as in Example 1 was carried out except that a styrene-butadiene cylindrical container (thickness: 2.2 mm) having an oxygen transmission rate of $2.1 \times 10^{-10}$ cm³·cm/(cm²·s·cmHg) was filled with a hollow-fiber membrane bundle.

The oxygen concentration within the container, which was measured 20 days after replacement with nitrogen, was 15%.

Comparative Example 3

The same method as in Example 1 was carried out except that a polypropylene cylindrical container (thickness: 0.65 mm) having an oxygen transmission rate of $2.5 \times 10^{-10}$ cm³·cm/(cm²·s·cmHg) was filled with a hollow-fiber membrane bundle.

The oxygen concentration within the container, which was measured 20 days after replacement with nitrogen, was 17%.

TABLE 1

|  | Example 1 | Example 2 | Example 3 | Example 4 | Example 5 | Example 6 | Example 7 |
|---|---|---|---|---|---|---|---|
| Amount (mg/m²) of lipid-soluble substance on inner surface of hollow-fiber membrane | 52 | 298 | 52 | 10 | 52 | 52 | 53 |
| Oxygen transmission rate (cm³·cm/(cm²·s·cmHg)) of container | $1.3 \times 10^{-10}$ | $1.1 \times 10^{-10}$ | $1.3 \times 10^{-10}$ | $1.5 \times 10^{-10}$ | $1.3 \times 10^{-10}$ | $1.3 \times 10^{-10}$ | $1.3 \times 10^{-10}$ |
| Oxygen concentration (%) in container after 20 days (one day in Example 6) | 8 | 5 | 2 | 10 | 1 or less | 1 | 9 |
| Absorbance of body of container at a wavelength of 350 nm | 0.66 | 0.12 | 0.66 | 0.14 | 0.66 | 0.66 | 0.66 |
| Hydrogen peroxide concentration (ppm) in initial discharge solution (100 mL) when saline is passed through | 5 ppm | 2 ppm | 1 ppm | 8 ppm | 0 ppm | 1 ppm | 7 ppm |

TABLE 1-continued

|  | Example 1 | Example 2 | Example 3 | Example 4 | Example 5 | Example 6 | Example 7 |
|---|---|---|---|---|---|---|---|
| Oxygen transmission rate ($cm^3 \cdot cm/(cm^2 \cdot s \cdot cmHg)$) of sterilizing bag | No sterilizing bag | No sterilizing bag | $1.5 \times 10^{-15}$ | No sterilizing bag | No sterilizing bag | No sterilizing bag | No sterilizing bag |
| Lactate dehydrogenase (LDH) activity ($\Delta abs/hr \cdot m^2$) | 13 ○ | 43 ○ | 9 ⊚ | 16 ○ | 7 ⊚ | 11 ○ | 15 ○ |
| Antioxidant capacity (mg/m²) | 46 ○ | 136 ○ | 49 ○ | 36 ○ | 57 ○ | 54 ○ | 44 ○ |
| Antioxidant capacity (mg/m²) when exposed to fluorescent light | 32 ○ | 64 ○ | 35 ○ | 19 ○ | 42 ○ | 39 ○ | 29 ○ |

TABLE 2

|  | Example 8 | Example 9 | Example 10 | Comparative Example 1 | Comparative Example 2 | Comparative Example 3 |
|---|---|---|---|---|---|---|
| Amount (mg/m²) of lipid-soluble substance on inner surface of hollow-fiber membrane | 18 | 52 | 52 | 350 | 52 | 52 |
| Oxygen transmission rate ($cm^3 \cdot cm/(cm^2 \cdot s \cdot cmHg)$) of container | $1.3 \times 10^{-10}$ | $1.8 \times 10^{-10}$ | $1.0 \times 10^{-10}$ | $1.3 \times 10^{-10}$ | $2.1 \times 10^{-10}$ | $2.5 \times 10^{-10}$ |
| Oxygen concentration (%) in container after 20 days | 1 or less | 10 | 6 | 8 | 15 | 17 |
| Absorbance of body of container at a wavelength of 350 nm | 0.84 | 0.36 | 1.00 | 0.66 | 0.32 | 0.26 |
| Hydrogen peroxide concentration (ppm) in initial discharge solution (100 mL) when saline is passed through | 8 ppm | 10 ppm | 4 ppm | 8 ppm | 15 ppm | 17 ppm |
| Oxygen transmission rate ($cm^3 \cdot cm/(cm^2 \cdot s \cdot cmHg)$) of sterilizing bag | No sterilizing bag | No sterilizing bag | No sterilizing bag | No sterilizing bag | No sterilizing bag | No sterilizing bag |
| Lactate dehydrogenase (LDH) activity ($\Delta abs/hr \cdot m^2$) | 45 ○ | 14 ○ | 12 ○ | 209 X | 67 X | 62 X |
| Antioxidant capacity (mg/m²) | 37 ○ | 47 ○ | 45 ○ | 112 ○ | 12 X | 13 X |
| Antioxidant capacity (mg/m²) when exposed to fluorescent light | 30 ○ | 27 ○ | 40 ○ | 99 ○ | 9 X | 10 X |

The present application is based on Japanese Patent Application No. 2014-199266 filed Sep. 29, 2014, the contents of which are incorporated herein by reference.

INDUSTRIAL APPLICABILITY

The hollow-fiber membrane blood purification device of the present invention has industrial applicability in a blood purification therapy.

REFERENCE SIGNS LIST

1 Hollow-fiber membrane for blood treatment
1a First flow path
2 Cylindrical container
2a, 2b Port
3a, 3b Sealing resin
6a, 6b Nozzle
7a Header cap
8 Inner space in header
10 hollow-fiber membrane blood purification device
11 Second flow path
Fa Flow direction of Fluid 1 (e.g., dialysis liquid)
Fb Flow direction of Fluid 2 (e.g., blood)

The invention claimed is:

1. A hollow-fiber membrane blood purification device obtained by filling a container with a hollow-fiber membrane, wherein
the hollow-fiber membrane comprises a hydrophobic polymer, a hydrophilic polymer and a lipid-soluble substance,
an amount of the lipid-soluble substance on the inner surface of the hollow-fiber membrane is 10 mg/m² or more and 300 mg/m² or less, and
an oxygen transmission rate of the container is $1.8 \times 10^{-10}$ $cm^3 \cdot cm/(cm^2 \cdot s \cdot cmHg)$ or less.

2. The hollow-fiber membrane blood purification device according to claim 1, wherein an absorbance of the body of the container at a wavelength of 350 nm is 0.35 or more and 2.00 or less.

3. The hollow-fiber membrane blood purification device according to claim 1, wherein a hydrogen peroxide concentration of an initial effluent (100 mL) when saline is passed through is 10 ppm or less.

4. The hollow-fiber membrane blood purification device according to claim 1, wherein the hollow-fiber membrane blood purification device is housed in a sterilizing bag having an oxygen transmission rate of $1.5 \times 10^{-10}$ $cm^3 \cdot cm/(cm^2 \cdot s \cdot cmHg)$ or less.

5. The hollow-fiber membrane blood purification device according to claim 1, wherein the lipid-soluble substance is a lipid-soluble vitamin.

6. The hollow-fiber membrane blood purification device according to claim 1, wherein the hydrophobic polymer has a solubility parameter $\delta(cal/cm^3)^{1/2}$ of 13 or less.

7. The hollow-fiber membrane blood purification device according to claim 1, wherein the hydrophobic polymer is at least one selected from the group consisting of polysulfone, polyethersulfone and cellulose triacetate.

8. The hollow-fiber membrane blood purification device according to claim 1, wherein the hydrophilic polymer is polyvinylpyrrolidone.

* * * * *